(12) United States Patent
Alexander

(10) Patent No.: US 9,433,485 B2
(45) Date of Patent: Sep. 6, 2016

(54) IMPLANT TENSION ADJUSTMENT SYSTEM AND METHOD

(71) Applicant: AMS Research, LLC, Minnetonka, MN (US)

(72) Inventor: James A. Alexander, Excelsior, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 14/846,927

(22) Filed: Sep. 7, 2015

(65) Prior Publication Data

US 2015/0374473 A1  Dec. 31, 2015

Related U.S. Application Data

(63) Continuation of application No. 13/229,460, filed on Sep. 9, 2011, now Pat. No. 9,125,717.

(60) Provisional application No. 61/445,840, filed on Aug. 23, 2011.

(51) Int. Cl.
*A61F 5/48* (2006.01)
*A61F 2/00* (2006.01)

(52) U.S. Cl.
CPC ............ *A61F 2/004* (2013.01); *A61F 2/0045* (2013.01); *A61F 2/0063* (2013.01); *A61F 2002/0068* (2013.01); *A61F 2220/0016* (2013.01); *A61F 2250/0003* (2013.01); *A61F 2250/0012* (2013.01); *A61F 2250/0013* (2013.01)

(58) Field of Classification Search
CPC .... A61F 2/004; A61F 2/0045; A61F 2/0063; A61F 2002/0068; A61F 2220/0016; A61F 2250/0003; A61F 2250/0012; A61F 2250/0013
USPC ................ 600/29–32, 37; 606/151–153, 157
See application file for complete search history.

(56) References Cited

U.S. PATENT DOCUMENTS

| | | | | |
|---|---|---|---|---|
| 6,039,686 A | * | 3/2000 | Kovac | A01H 5/02 600/30 |
| 7,395,822 B1 | * | 7/2008 | Burton | A61F 2/004 128/885 |

* cited by examiner

*Primary Examiner* — Samuel Gilbert
(74) *Attorney, Agent, or Firm* — Brake Hughes Bellermann LLP

(57) ABSTRACT

An implant or sling device is provided with a tension adjustment system. The adjustment system can include one or more fluid reservoirs to facilitate tension adjustment. Various conduits, balloons, introduction tools, ports and fluid adjustment components and mechanisms can be included to provide selective adjustment of the tension of the implant relative to the supported tissue or organ.

20 Claims, 5 Drawing Sheets

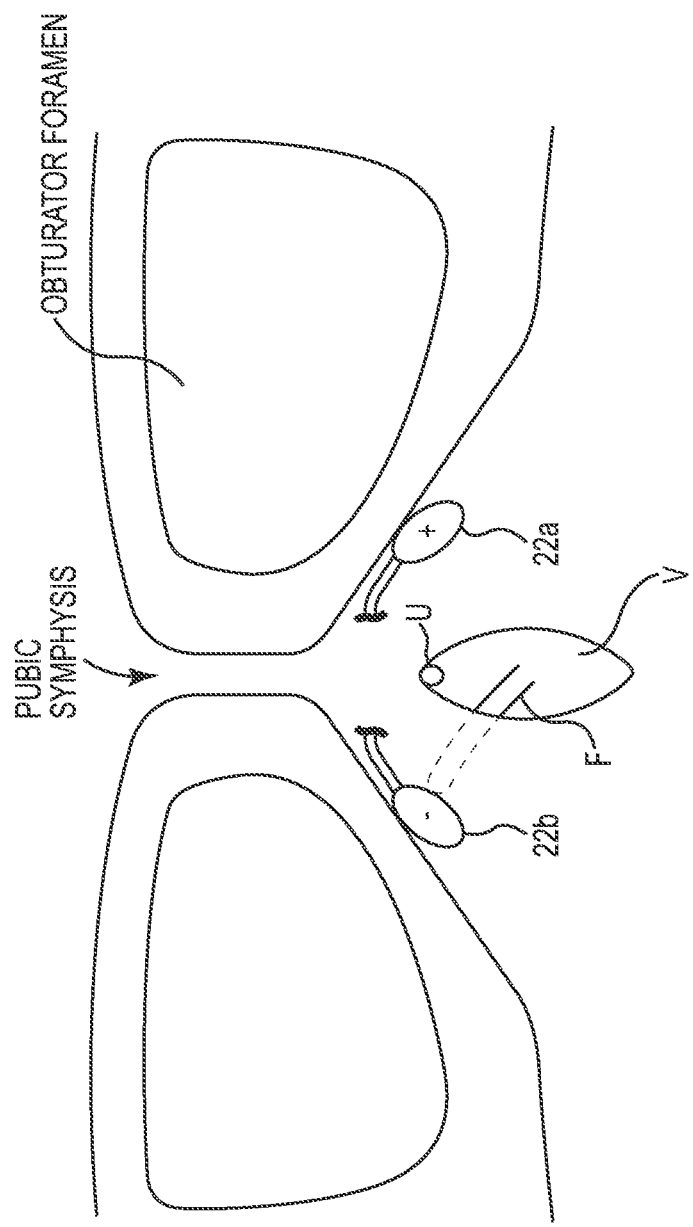

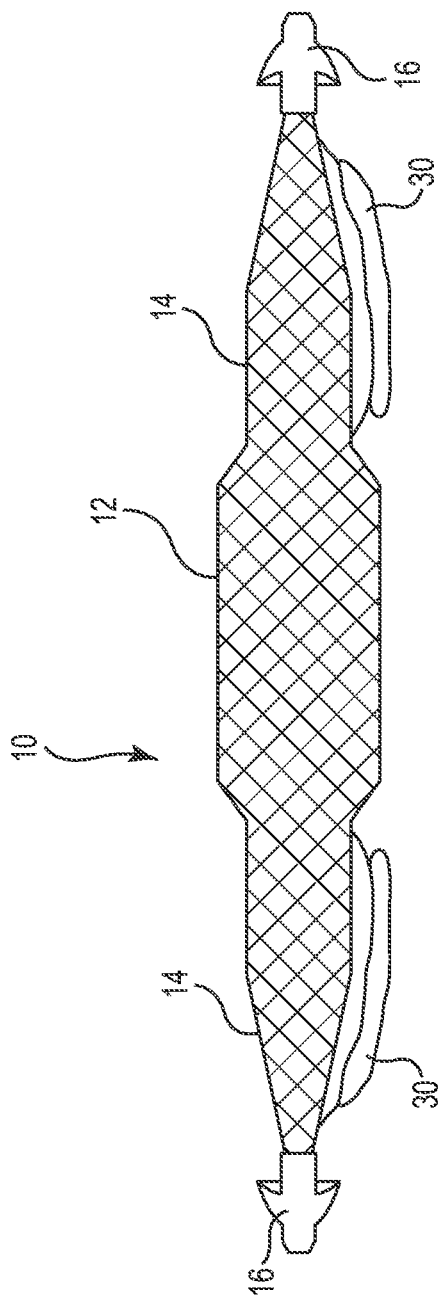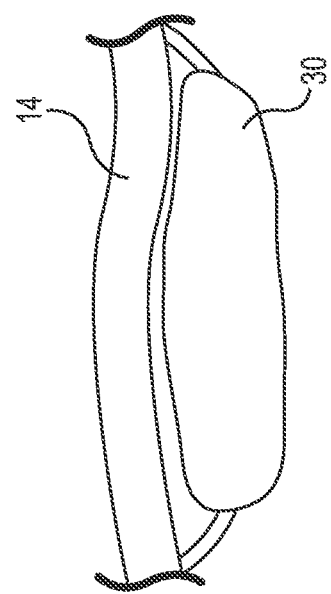

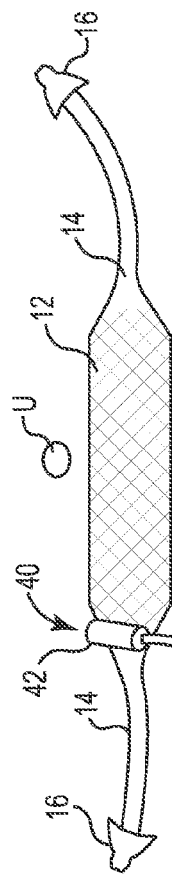
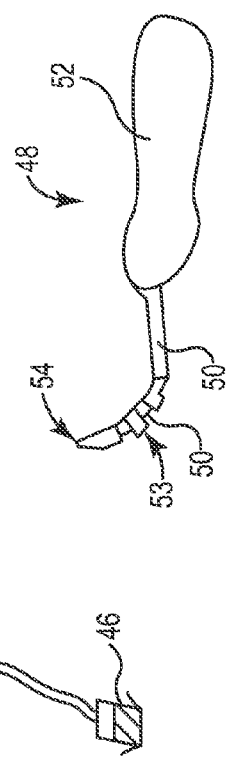
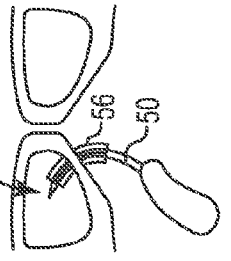
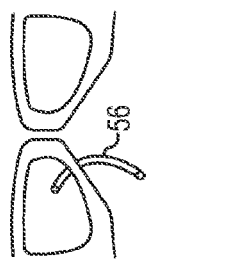
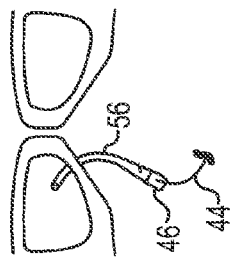
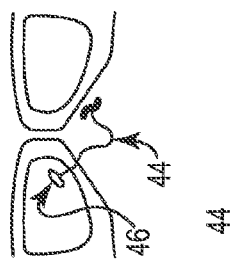

IMPLANT TENSION ADJUSTMENT SYSTEM AND METHOD

PRIORITY

This Application is a Continuation Application of U.S. application Ser. No. 13/229,460, filed Sep. 9, 2011, which claims priority to and the benefit of U.S. Provisional Application No. 61/445,840, filed Feb. 23, 2011, each of which is incorporated fully herein by reference in its entirety.

FIELD OF THE INVENTION

The present invention relates generally to surgical methods and apparatus and, more specifically, to a post-implant tension adjustment systems and methods.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

With convention systems and methods, the challenge is with adjusting tension of the sling or implant after the deployment and positioning procedure is complete. It can be difficult to access the implant and increase or decrease tension to improve the patient's outcome.

There is a desire to obtain a minimally invasive yet highly effective system and method of adjusting the urethra or other anatomical pelvic structure or tissue after a mesh implant or like device has been implanted.

SUMMARY OF THE INVENTION

The present invention describes systems and methods of adjusting the urethra or like anatomical structures after implantation of pelvic slings or implants to treat incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness (male and female).

The adjustment system can include two or more small pressure bulbs placed against an endopelvic structure, e.g., the inferior pubic rami, for support. By palpating the bulbs (e.g., bilaterally—one on left and one on right), the pressure can be adjusted without any incisions. The pressure increments, increasing or decreasing, can be relatively minor in order to fine tune the corrective tension of the implant on the urethra. The system can also include one or more check valves and two small reservoirs. At least one of the check valves can be spring loaded on a release side of the system to prevent over-pressurizing of the system.

The implant support portion introduced and deployed beneath the urethra is generally flat to prevent local pressure points on the supported tissue or structure. In addition, this urethra support can be temporarily attached to a manometer to provide feedback on the tension during the procedure. Once the manometer is removed, that port is sealed automatically to prevent leakage.

Various embodiments can include elongate inflation conduits or balloons extending along a portion of the implant, such as the extension portions. As such, inflation or deflation of the conduits or balloons with correspondingly adjust the length or spanning distance of the extension portions to adjust tension of the implant relative to the supported tissue or organ.

Other embodiments can include a fluid or adjustment device provided with the implant, and a conduit extending from the adjustment device to an opposing or distal injection port. An introduction tool and hollow tube assembly can be implemented to deploy the injection port within the patient to provide a port to later facilitate control over the adjustment device to control tension of the implant relative to the supported tissue or organ. The injection port can be anchored to tissue within the pelvic region of the patient.

The various fluid reservoirs, balloons, and inflation and adjustment devices described herein can be included along any portion of the implant 10 to facilitate tension adjustment, including the extension portions and the support portion of the implant. Tension is generally adjusted via displacement of the implant up or down, or by selectively controlling the length or spanning shape of the implant from end to end.

BRIEF DESCRIPTION OF THE DRAWINGS

FIG. 2 depicts a schematic view of internal palpation of components of an implant having a tension adjustment system in accordance with embodiments of the present invention.

FIG. 3-4 depict an implant having a tension adjustment system, with elongate fluid conduits, in accordance with embodiments of the present invention.

FIG. 5 depicts an implant having a tension adjustment device, a conduit and an injection port in accordance with embodiments of the present invention.

FIG. 6 depicts an introduction tool in accordance with embodiments of the present invention.

FIGS. 7-10 depict steps of deploying at least the injection port in accordance with the embodiments of FIG. 5.

DETAILED DESCRIPTION OF PREFERRED EMBODIMENTS

Figure 1:
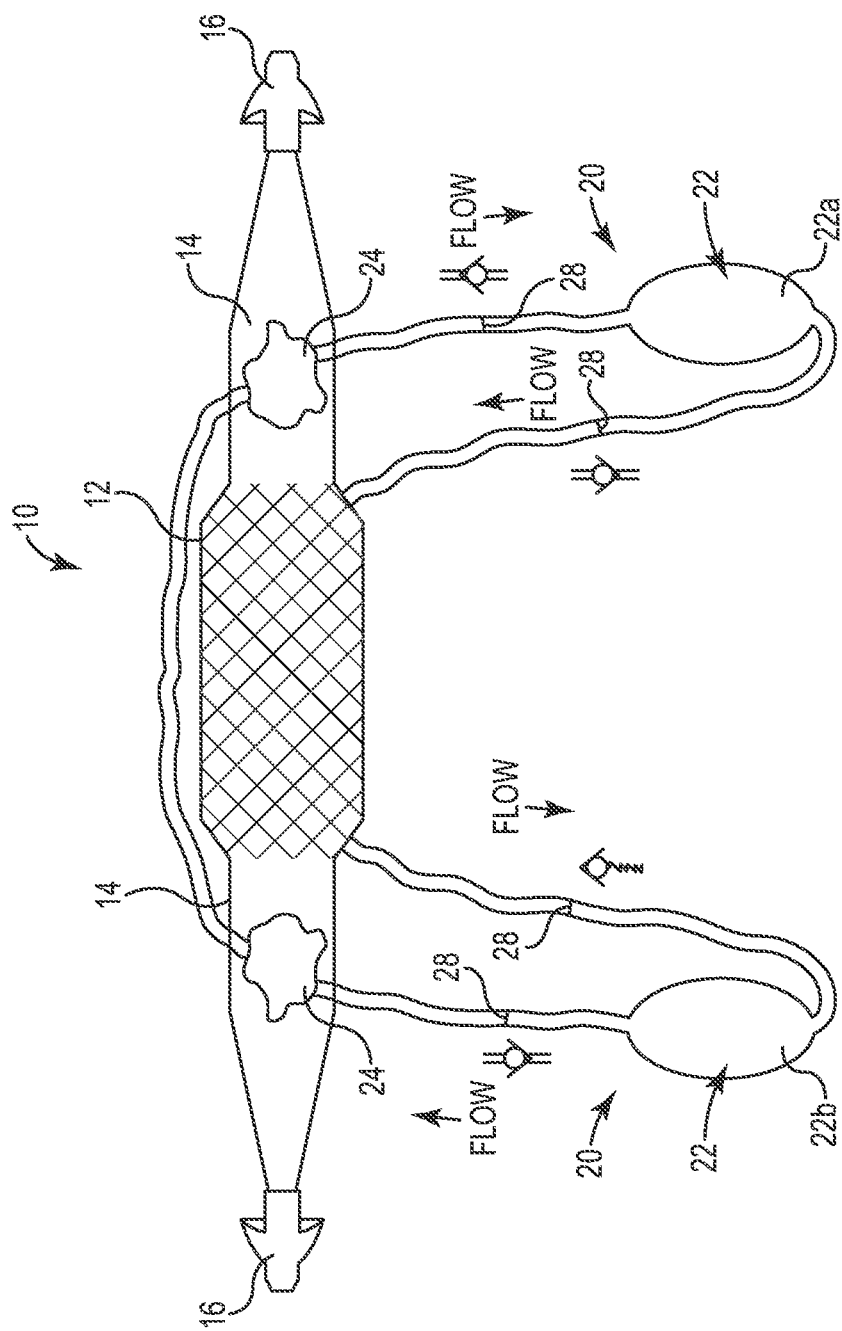
FIG. 1 depicts an implant having a tension adjustment system in accordance with embodiments of the present invention.

Referring generally to FIGS. 1-11, various embodiments of an adjustable implant system 10 and method are provided for use after a sling or implant deployment and positioning procedure, to treat pelvic conditions such as incontinence (male or female) or prolapse. In general, the implants 10 can include a tissue support portion 12, extension portions 14, and a pressure adjustment system or mechanism 20. The implants 10 can further include one or more anchor portions 16. The extension portion 14 can be included to span between or link the support portion 12 and the respective anchoring portions 16. Various portions of the implant 10 can be constructed of polymer materials, e.g., woven, shaped, molded or otherwise formed into or from a generally planar film or sheet material. Examples of acceptable polymer materials available in constructing or forming the implant systems 10 and its components can include polypropylene, polyethylene, fluoropolymers or like biocompatible materials.

Portions of the implant 10, such as the support portion 12, can be formed of a mesh material (woven or non-woven), or formed or patterned by way of a polymer molding process to create a unitary generally homogeneous non-woven, or non-knitted, device or construct. Other embodiments can be formed from an already unitary homogeneous sheet or film via laser cutting, die cutting, stamping and like procedures. Further, various embodiments of the implant 10 can be constructed of opaque, or translucent, polymer materials. The support portion 12 is generally adapted to support tissue, such as that required to treat urinary or fecal incontinence, including the bladder neck, urethra or rectum.

The various implants 10, structures, features and methods detailed herein are envisioned for use with many known implant and repair devices (e.g., for male and female urinary and fecal incontinence solutions), features and methods, including those disclosed in U.S. Pat. Nos. 7,500,945, 7,407,480, 7,351,197, 7,347,812, 7,303,525, 7,070,556, 7,025,063, 6,911,003, 6,802,807, 6,702,827, 6,691,711, 6,652,450, 6,648,921, and 6,612,977, International Patent Publication Nos. WO 2011/072148, WO 2008/057261 and WO 2007/097994, and U.S. Patent Publication Nos. 2011/0124956, 2010/0261955, 2004/0039453, 2002/0151762 and 2002/0147382. Accordingly, the above-identified disclosures are fully incorporated herein by reference in their entirety.

The adjustable implant system 10 can be attached to or otherwise provided with a sling device (such as a mesh incontinence sling) as shown in FIG. 1. The adjustment system 20 can include an inflation system having one or more small pressure bulbs 22 and one or more bladder or reservoir portions 24. Portions of the inflation system, such as the bulbs 22 can be placed against or proximate the inferior pubic rami for support. Various tubes or conduits 26 can be provided to facilitate fluid and operable communication along the system 20 components. The fluid contents of the system 20 can include gas, liquid, gel, and like materials or substances. With such a system 20, tension adjustment can occur days, weeks, month, or even years after implantation of the implant 10. Such a system 20 further permits tension adjustment without requiring invasive external abdominal incisions.

By palpating the bulbs 22 (e.g., bilaterally—a bulb 22a on the right and a bulb 22b on the left), the pressure can be adjusted without any incisions. The pressure increments and decrements can be relatively minor and variable. For instance, the pressure increments can be controlled according to the volumetric and material deformation properties of the bulbs 22, bladders 24 or conduits 26. This can provide fine tuned displacement of a portion of the implant 10 (e.g., extension portions 14) and, in turn, the tension of the implant 10 on the urethra or other anatomical structure or surrounding tissue. The system 10 can also include one or more check valves 28 to provide better control over the intake and release of the fluid pressure. At least one check valve 28 can be spring loaded on a release side of the system to prevent over-pressurizing of the system. In various embodiments, the check valves 28 can be included in the communication with, or within, the conduits 26 or other system 20 components.

FIG. 1 depicts fluid flow and pressure control layouts for embodiments of the present invention. In one embodiment of use, the bilateral configuration of the pressure adjustment system 20 includes use of the bulb 22a and corresponding bladder or reservoir 24 and/or conduits 26 as a pressure increase side, and the bulb 22b and respective components can serve as the pressure release side. Implant tension and positioning adjustment can occur post-procedure. With the system 20 components provided and maintained within the endopelvic space at the time of the implantation procedure, later adjustments can be made through palpation or pressure upon external or internal trigger points or zones, e.g., abdominal, vaginal, perennial, and the like. A physician, or other individuals, can apply pressure or use a finger F to palpate the desired bulb device 22 to control an increase or decrease of pressure in the respective reservoir 24. Tools or other devices can also be utilized to activate or apply pressure to the target bulb device 22 in certain embodiments.

Again, the bulbs 22 can be placed in abuttable contact or positioning with a resistive anatomical structure, such as the pubic bone or like structure. A pressure increase in the pressure adjustment system 20 will generally cause displacement of the implant 10 such that tension is increased on the supported tissue, such as the urethra. A pressure decrease to the pressure adjustment system 20 will generally cause the implant to withdraw a measurable degree to reduce tension on the supported tissue. The correlation between the pressure increase/decrease and the direction of the implant 10 displacement can vary depending on the location of the reservoirs 24 (e.g., top or bottom surface of the implant 10) relative to the supported and surrounding tissue.

FIG. 2 depicts an exemplary method of using a finger F inserted within the vaginal opening V to access and activate the respective bulbs 22 against the pubic bone region of the patient to control the pressure (e.g., tension of the implant 10 on the urethra U).

A manometer or other like device can be included (e.g., temporarily) in operable communication with the system 20 to provide feedback on the tension during the tensioning procedure. The manometer can be selectively ported to a portion or component of the system 20 such that the port can be sealed automatically to prevent leakage or a pressure breach after use.

Other embodiments of the present invention are depicted in FIGS. 3-4. In such embodiments, the pressure adjustment system 20 can include one or more elongate balloons or conduits 30. The conduits 30 can be positioned longitudinally along a side or surface of the implant 10 such that fluid or like pressure within the conduits 30 can be selectively controlled (increased or decreased incrementally or variably) to displace a portion of the implant 20 to control tension. In certain embodiments, the conduits 30 are positioned along and adjacent the extension portions 14 of the implant. Again, the support portion 12 is generally adapted to remain flat to avoid pressure points against the supported tissue or anatomical structure. However, in certain embodiments, various channels or conduits can extend within or along the support portion 12 in communication with the other conduits, reservoirs or components of the system 20.

FIG. 4 depicts one of the conduits 30 in an increased pressure state (inflated) to displace the extension portion 14 accordingly to adjust tension. As the conduits 30 are inflated, the conduits 30 expand and shorten to increase tension by shortening the span of length of the respective expansion portion 14. The conduits 30 can be in operable fluid communication with each other to facilitate traversal of the fluid pressure from one side to the other. Alternatively, each conduit 30 (bilateral placement along extension portions 14) can be isolated such that each is subject to separate pressure adjustment. Various tubes and other conduits can be included to facilitate traversal and storage of fluid or like substances or materials such that the conduits 30 can operate as generally elongate reservoirs. Inflation of the conduits 30 can be facilitated with the introduction of a tool or device adapted to introduce liquid, air or like contents in or out of the conduits 30. In one embodiment, the tool can be introduced via a vaginal incision for access to the conduits 30 after the implantation of the implant 10. Other embodiments can include manual palpation as described herein.

The construct of the reservoirs, conduits, tubes, and like components of the adjustment systems 20 can vary greatly depending on the desired application and adjustment needs. For instance, various polymers, metals and like materials can be utilized to construct the components to facilitate the desired flexibility, rigidity, deformation and fluid communication objectives of the particular pressure adjustment embodiments.

Referring generally to FIGS. 5-10, an embodiment of an adjustment system or mechanism 40 is shown. The system 40 can include one or more inflation or adjustment devices 42, one or more conduits or tubes 44 and an injection port 46. The injection port 46 and conduit 44 are in operable fluid communication with the adjustment device 42. In various embodiments, a separate device 42, conduit 44 and port 46 can be included on each extension portion 14 side of the implant 10.

A tool or other device can dock with the implanted injection port 46 to control fluid, pressure or other selective displacement of the adjustment device 42 to control tension of the implant 10 relative to the supported tissue (e.g., urethra). The injection port 46 can include one or more tines or anchoring features to facilitate tissue anchoring of the port 46 within the pelvic region such that the port 46 is accessible (e.g., via vaginal incision) to later adjust the tension. In certain embodiments, the injection port 46 is anchored to muscles, ligaments or fascia proximate the urethra, such as the obturator foramen, internus, membrane or like anatomical tissue or structures.

An insertion and deployment tool 48 can include a flexible needle portion 50 and a handle portion 52. The needle portion 50 can include a flex portion 53, a distal tip 54 (e.g., sharp or blunt), and an outer sleeve or hollow channel tube 56. The tube 56 includes a lumen therethrough adapted to receive and pass the port 46 through. The tube 56 can be c-shaped, enclosed, or take on a variety of other shapes to facilitate deployment and use to pass the port 46. In certain embodiments, a groove or like slot along the length of the tube 56 will facilitate routing of the conduit 44 as the port 46 is passed through the length of the tube 56.

Upon implantation of the sling or implant 10, including the methods of the above-incorporated references, the exemplary deployment steps shown in FIGS. 7-10 for the injection port 46 and conduit 44 can be performed. First, the needle portion 50 of the tool 48 is inserted through a vaginal incision to obtain endopelvic access. The needle portion 50 can carry the hollow tube 56 such that the tip 54 is directed through to target tissue (FIG. 7), such as the obturator internus membrane. The needle portion 50 can be flexible to facilitate this manipulation. From there, the flexible needle 50 is withdrawn to leave the hollow tube 56 is the desired place and orientation for introduction of the port 46 (FIG. 8). The needle 50 can be withdrawn or disengaged from the hollow tube 56 via manual manipulation or a mechanical actuator in the handle 52. The port 46 is then inserted or deployed through a proximal end of the tube 56 and directed up or along the tube 56 (e.g., via tool 48 or another tool or device) for placement, e.g., anchoring within the target tissue or anatomical structure (FIG. 9). The port 46 includes the extending conduit 44 for communication with the device 42 to control tension. The tube 56 can then be withdrawn to leave the port 46 and extending conduit 44 in place (FIG. 10). Tools, devices and techniques can then be used to dock with the injection port 46 to selectively control expansion, retraction or displacement of the adjustment device 42 to control the tension of the implant 10. For instance, a fluid device can dock with the port 46 to introduce fluid into, or withdrawal fluid from, the device 42. Various embodiments of the process can further include later accessing or docking with the implanted port 46 or conduit 44 readily accessible via a vaginal incision to adjust the tension days, weeks, months or even years after implantation.

The injection 46 and conduit 44 configuration of the adjustment system 40 can also be employed with other embodiments of the present invention to provide the desired post-procedure pressure control (inflation and deflation) system, including the embodiments of FIGS. 1-2 and FIGS. 3-4. Such a pressure and tension adjustment system can serve as an alternative system and technique from finger or manual palpation.

Figure 11:
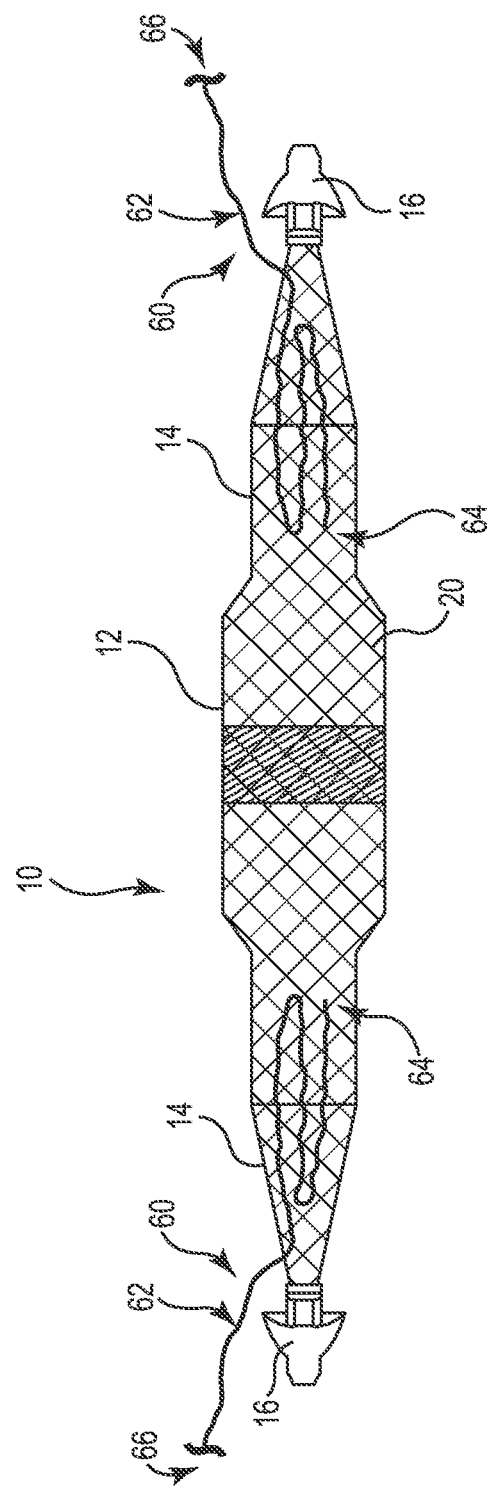
FIG. 11 depicts an implant having a suture pulley tension adjustment system in accordance with embodiments of the present invention.

FIG. 11 shows an embodiment of the system 10 having one or more pulley member or suturing systems 60 having one or more interwoven or looped members or sutures 62 adapted to impose selective elongation and contraction of the implant 10 to provide urethral and sling device adjustment. Various sutures, structures, devices and mechanisms can be employed to achieve the various adjustment devices and components described and depicted herein. A first end 64 of the suture system 60 can be anchored or provided with the implant 10 with a length of the suture 62 looping or traversing a pattern in the implant 10 such that a second end 66 extends out from the implant 10. Pulling on or otherwise extending the second end 66 away from the implant 10 can shorten or buckle a portion of the implant 10, such as the extension portion 14, to increase tension or raise the implant relative to supported tissue Likewise, releasing the length of the suture 62 back toward the implant 10 can serve to release tension for the implant 10.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An adjustable pelvic implantation method, comprising:
providing an elongate implant having a support portion, at least one extension portion extending from the support portion and having a tissue anchor, and at least one fluid reservoir portion, with the at least one fluid reservoir portion provided generally adjacent to the at least one extension portion;
placing the elongate implant against pelvic tissue; and selectively inflating the at least one fluid reservoir portion to adjustably expand and increase tension by shortening a span of the at least one extension portion to facilitate support of the pelvic tissue.

2. The method of claim 1, further including providing a flexible conduit in communication with the at least one fluid reservoir.

3. The method of claim 1, wherein the tissue anchor includes extending tines.

4. The method of claim 1, wherein the support portion is adapted to support a urethra.

5. The method of claim 1, wherein the support portion is adapted to support a rectum.

6. The method of claim 1, wherein the support portion is adapted to support a bladder neck.

7. The method of claim 1, wherein the elongate implant is constructed at least in part of an elongate porous mesh material.

8. The method of claim 1, wherein the elongate implant is constructed of a woven mesh material.

9. The method of claim 1, wherein the elongate implant is constructed at least in part of a non-woven, generally homogenous polymer material.

10. The method of claim 1, wherein the at least one extension portion includes a first and a second extension portion.

11. The method of claim 10, wherein the implant further includes a second fluid reservoir portion provided generally adjacent to the second extension portion.

12. An adjustable pelvic implantation method, comprising:
providing an elongate implant having a support portion, first and second extension portions each extending laterally from the support portion and having a tissue anchor, and a first and second fluid reservoir portions, with the first fluid reservoir portion provided generally adjacent to the first extension portion of the implant and the second fluid reservoir portion provided generally adjacent to the second extension portion;
placing the elongate implant against pelvic tissue; and
selectively inflating at least one of the first and second fluid reservoir portions to adjustably expand and increase tension by shortening a span of at least one of the first and second extension portions to facilitate support of the pelvic tissue.

13. The method of claim 12, further including providing a first flexible conduit in communication with the first fluid reservoir portion.

14. The method of claim 12, further including providing a second flexible conduit in communication with the second elongate fluid reservoir portion.

15. The method of claim 12, wherein the support portion is adapted to support a urethra.

16. The method of claim 12, wherein the support portion is adapted to support a rectum.

17. The method of claim 12, wherein the support portion is adapted to support a bladder neck.

18. The method of claim 12, wherein the elongate implant is constructed of a woven mesh material.

19. The method of claim 12, wherein the elongate implant is constructed at least in part of a non-woven, generally homogenous polymer material.

20. The method of claim 12, wherein the support portion has a width dimension greater than a width dimension of at least one of the first and second extension portions.

* * * * *